United States Patent
Cho et al.

(10) Patent No.: US 7,483,140 B1
(45) Date of Patent: Jan. 27, 2009

(54) MICRO INTEGRATED PLANAR OPTICAL WAVEGUIDE TYPE SPR SENSOR

(75) Inventors: Hyoung Jin Cho, Oviedo, FL (US); Hyungseok Bang, Orlando, FL (US); Patrick Li Kam Wa, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 326 days.

(21) Appl. No.: 11/297,750

(22) Filed: Dec. 8, 2005

Related U.S. Application Data

(60) Provisional application No. 60/635,725, filed on Dec. 10, 2004.

(51) Int. Cl.
  *G01N 21/55* (2006.01)
(52) U.S. Cl. ...................... 356/445; 356/448
(58) Field of Classification Search ......... 356/630–632, 356/432–435, 445–448; 382/144–145; 250/559.1–559.28
See application file for complete search history.

(56) References Cited

U.S. PATENT DOCUMENTS

| | | | |
|---|---|---|---|
| 5,313,264 A | 5/1994 | Ivarsson et al. ............... 356/73 |
| 5,359,681 A | 10/1994 | Jorgenson et al. ............. 385/12 |
| 5,478,755 A | 12/1995 | Attridge et al. ............. 436/518 |
| 5,485,277 A * | 1/1996 | Foster ......................... 356/445 |
| 5,841,143 A | 11/1998 | Tuma et al. ............... 250/458.1 |
| 5,955,729 A | 9/1999 | Nelson et al. ............... 250/282 |
| 6,111,652 A | 8/2000 | Melendez et al. ........... 356/445 |
| 6,183,696 B1 | 2/2001 | Elkind et al. ............. 422/82.05 |
| 6,424,418 B2 * | 7/2002 | Kawabata et al. ........... 356/445 |
| 6,469,785 B1 | 10/2002 | Duveneck et al. ........... 356/244 |
| 7,285,420 B2 * | 10/2007 | Fontaine et al. ............. 436/164 |
| 7,295,294 B2 * | 11/2007 | Shimazaki .................... 356/128 |
| 2003/0077642 A1 | 4/2003 | Malmqvist et al. |
| 2003/0077842 A1 | 4/2003 | Malmqvist et al. .......... 436/518 |
| 2003/0226604 A1 | 12/2003 | Schlautmann et al. ....... 137/827 |
| 2004/0072278 A1 | 4/2004 | Chou et al. .................... 435/29 |
| 2004/0112529 A1 | 6/2004 | Karlsson et al. .......... 156/306.6 |
| 2005/0018949 A1 * | 1/2005 | Yan .............................. 385/14 |

* cited by examiner

*Primary Examiner*—Gregory J Toatley, Jr.
*Assistant Examiner*—Tri T Ton
(74) *Attorney, Agent, or Firm*—Brian S. Steinberger; Phyllis K. Wood; Law Offices of Brian S. Steinberger, P.A.

(57) ABSTRACT

An integrated optical waveguide type surface plasmon resonance (SPR) sensor having an optical waveguide with a corresponding SPR sensing area, photodetectors, and wavelength tunable laser or any kind of external tunable laser source/coupler formed on a substrate. In an embodiment, the laser is a wavelength tunable laser and optionally, the integrated device may include a power source on the substrate for providing a electric power to the wavelength tunable laser and the photodetectors, or a circuit for signal processing, or a microfluidic structure for routing a target sample to the SPR sensor area. The microfluidic structure optionally includes a mixer or a reaction chamber for mixing and allowing a physical or chemical reaction to occur, respectively. In an embodiment, plural planar integrated optical waveguide type SPR sensors may be fabricated on a substrate to form an array of SPR sensors.

21 Claims, 14 Drawing Sheets

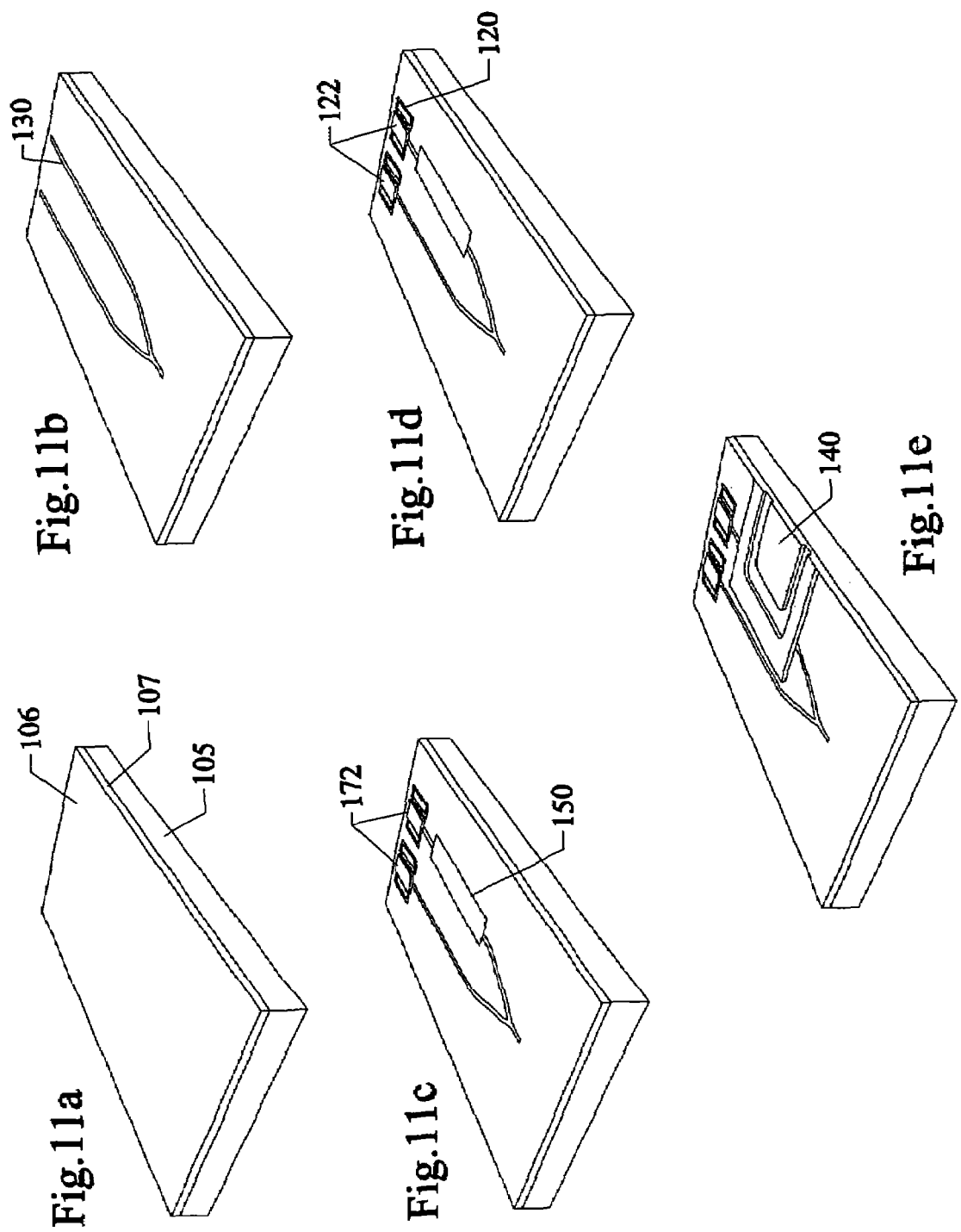

MICRO INTEGRATED PLANAR OPTICAL WAVEGUIDE TYPE SPR SENSOR

This application claims the benefit of priority to U.S. Provisional Patent Application No. 60/635,725 filed on Dec. 10, 2004.

FIELD OF THE INVENTION

This invention relates to surface plasmon resonance sensors and, in particular, to methods, systems, apparatus and devices for integrating the optical waveguide, photodector, surface plasmon resonance (SPR) detection layer, and optionally included microfluidic structure on a single substrate to provide a micro integrated planar optical waveguide type surface plasmon resonance sensor.

BACKGROUND AND PRIOR ART

Basic working principle of surface plasmon resonance (SPR) sensor is inducing a spectrum of light into a sensing region and analyzing the absorption spectrum from the sensing region. Generally, inducing a spectrum of light on a sensing layer can be achieved in two ways; shining single wavelength of light with a range of incident angle or inducing a wavelength range of light. Sensor type is divided into two correspondingly; reflection type and waveguide type.

The reflection type SPR sensor 10, as shown in FIG. 1, works by applying single wavelength of light on the back side of a sensing layer with a range of angle and measuring the shifted amount of minimum light reflection angle before and after an analyte is induced to detection layer. The minimum light reflection angle is related with analyte's refractive index and detection layer metal. If the refractive index of analyte changes, the refractive index change would be reflected on the shift of minimum reflection angle. A conventional and commercially available SPR sensor 10 consists of optical components including a light source that produces a polarized light 12, a prism 14, and a CCD array 18. The metal film 22 is prepared to have a functionalized surface for the adsorption of biochemical molecules from a fluidic sample 24. The light source generates a polarized light 12 which is directed through the prism 14, striking the metal film 22. Reflected light 16 is detected by the CCD array 18. As the fluid sample 24 passes through the fluidic channel 26, the binding of the molecules changes the refractive index, which is monitored, conventionally, by the shift of the minimum reflection angle.

An advantage of the reflector SPR sensor is that it may include plural interactive surfaces, metal films 22, to allow a multiple channel analysis of the sample 24. However, a disadvantage of the reflector sensor is that the sensor is not fully integrated on a planar surface. Instead, optical components are located a distance from the planar surface to provide a polarized light that strikes, and is reflected from, the metal film 22. Since the reflector type sensor is based on the measurement of the reflected light intensity, the CCD array for monitoring minimum light reflection peak is also located outside the plane. Thus, the reflector SPR sensor is "bulky".

Miniaturized reflector type SPR sensors are disclosed in U.S. Pat. Nos. 6,183,696 issued to Elkind et al on Feb. 6, 2001 and 6,191,847 issued to Melendez et al. on Feb. 20, 2001. The miniaturized sensors include a substrate which provides a sensor platform to which a light transmissive housing is coupled, substantially encapsulating the sensor platform. A light source is provided above the platform or on the platform substrate and includes a polarizer for producing the polarized light that strikes an SPR layer which is formed on the exterior surface of the housing. A mirror, also located on the interior surface of the housing, deflects the light reflected from the SPR layer to a detector located on the sensor platform. The miniaturized reflector SPR sensor disclosed in the prior art may also include a power source, conversion electronics and a communication interface on the platform. Although most of the components are located on the platform, the housing is still necessary for contacting the target sample and reflecting the polarized light to the detector. While the overall size of the reflective SPR sensor is reduced, the resulting device is still bulky.

Another type of SPR sensor is waveguide type, which includes optical fiber type waveguide and planar waveguide. Fiber optic waveguides have a number of advantages over the bulkier prism-based sensors. Primarily, they can perform long distance detection for medical or otherwise sterile tasks. Fibers are also very small and have no moving parts, giving them a much broader range and making multiple sensor arrays a possibility.

A surface plasmon resonance sensor including plural optical waveguides and corresponding SPR sensor areas that permits the excitation of surface plasmons and plural fluidic channels is disclosed in U.S. Pat. No. 6,373,577 issued to Bräuer et al. on Apr. 26, 2002. In the Bräuer patent, an array of SPR waveguides are manufactured using technologies from semiconductor production and from integrated optics to provide plural parallel sensors on a single substrate located at a predefined distance from one another. Each strip-like optical waveguide that is expected to contact the sample fluid has at least one SPR sensor area including a metal layer that permits the excitation of surface plasmons. While the optical sensor disclosed in Bräuer provides plural waveguides with SPR surface areas and plural fluidic channels, external out-of-plane components are required to use the Bräuer optical sensor, namely, a light source, photodetectors and electronic components associated with operating the measurement device to which they are interfaced.

An alternative optical SPR detection device that is based on semiconductor laser array is disclosed in U.S. Pat. No. 6,469,785 issued to Duveneck et al. on Oct. 22, 2002. The Duveneck device comprises at least one light source, photodetector, an optical waveguide with a corresponding SPR area, and a fluidic channel in a single housing. The light source is a surface-emitting semiconductor laser located on a bottom substrate with the photodetector. An intermediate substrate above and separate from the bottom substrate includes at least one coupling-in grating and one coupling-out grating for coupling-in the emitted light from the surface-emitting laser to the optical waveguide and coupling-out to the photodetector. The optical waveguide includes a SPR surface area which contacts the target sample. A third substrate may be included a distance above the second substrate to form a fluidic reservoir for holding the target sample while in contact with the SPR sensor area.

While the Duveneck device may be enclosed to form a single unit, the device is bulky since the device requires a first substrate for the light source and detector and a separate second substrate for the coupling-in and coupling-out gratings, optical waveguide and corresponding SPR surface area. In an embodiment, the first, second and optional third substrate are enclosed in a housing with each substrate separated a predefined distance. In a second embodiment, the second substrate with the sensor layer is removable from the light source and detector on the first substrate. In still another embodiment, optical waveguides, such as an optical cable, are used to pass the light from the light source on the first substrate to the waveguide on the second substrate and back to the photodetector, thereby controlling the beam of the light. In the later embodiment, the first substrate may be located a further distance from the second substrate.

SUMMARY OF THE INVENTION

A first objective of the present invention is to provide methods, systems apparatus and devices that integrate light source and detection system and sensing layer and reduce the size of SPR sensor.

A second objective of the present invention is to provide methods, systems apparatus and devices to make planar SPR sensor structure and provide the availability of full integration of planar microfluidic components to the substrate.

A third objective of the present invention is to provide methods, systems apparatus and devices to allow for batch fabrication of the planar integrated optical waveguide type SPR sensor to reduce product cost.

A fourth objective of the present invention is to provide methods, systems apparatus and devices to make planar simple-structured SPR sensor and provide flexibility in fabrication.

A fifth objective of the present invention is to provide methods, systems apparatus and devices to remove external optical components and eliminate optical component alignment problem.

The methods, systems, apparatus and devices of the present invention advance the art by providing an integrated surface plasmon resonance (SPR) sensor comprising a substrate having an optical waveguide having a first end and a second end fabricated on the substrate, a light source coupled with the first end of the optical waveguide, at least one photodetector formed on the substrate coupled with the second end of the optical waveguide, at least one SPR sensor area formed to couple with a section of the optical waveguide between the light source and the at least one photodetector. A microfluidic structure having an inlet and an outlet can be optionally fabricated on the substrate for receiving a target sample, routing the target sample into contact with the at least one SPR sensor area and extracting the target sample, wherein the optical waveguide routes a light from the light source past the at least one SPR sensor area which evanescently penetrates the at least one SPR sensor area. In an embodiment, plural integrated SPR sensors may be integrated on a single substrate.

The light for detection may be induced from an integrated light source on the substrate or external light source coupled with optical fiber or any other types of optical coupler. Optionally, a fluidic structure having an inlet and outlet fluidic path and one or more of a reaction chamber and a mixer micro pump are formed on the substrate for routing the target sample. The integrated SPR sensor may also include a power source or a connection for receiving power and a user interface or a controller for controlling the integrated SPR sensor.

The present invention also provides a method for fabricating an integrated optical waveguide type surface plasmon resonance (SPR) sensor. The method includes providing a substrate, forming an optical waveguide on the substrate for routing a light from a light source to a photodector, forming a SPR sensor in contact with a section of the optical waveguide, forming an optical fluidic structure on the substrate to route a target sample past the SPR sensor, and forming the photodetector on the substrate that is coupled with the optical waveguide.

Further objects and advantages of this invention will be apparent from the following detailed description of preferred embodiments which are illustrated schematically in the accompanying drawings.

BRIEF DESCRIPTION OF THE FIGURES

FIGS. 11a-11i are perspective views of the planar integrated optical waveguide type SPR sensor at different steps of the fabrication process.

DESCRIPTION OF THE PREFERRED EMBODIMENTS

Figure 1:
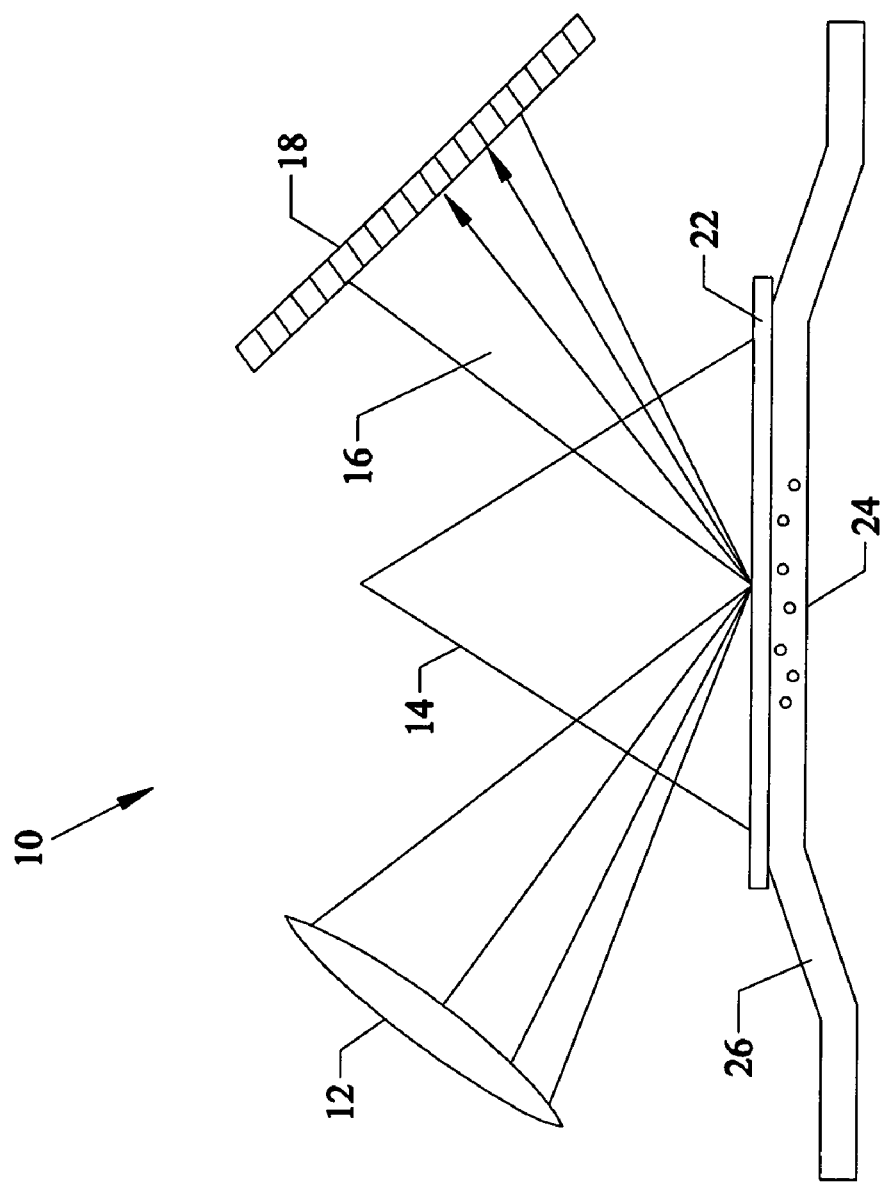
FIG. 1 is a side view of a bulky reflection type SPR according to the prior art.

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

The following is a list of the reference numerals used in the drawings and the detailed specification to identify components. In the description of the preferred embodiments and the figures, like components are identified by like reference numerals.

10 reflector type SPR sensor
12 polarized light
14 prism
16 reflected light
18 CCD array
22 metal film
24 fluidic sample
26 fluidic channel -continued

| | |
|---|---|
| 100 | planar integrated optical waveguide SPR sensor |
| 105 | substrate |
| 106 | SiON Layer |
| 107 | SiO₂ layer |
| 110 | wavelength tunable laser |
| 120 | photodetectors |
| 122 | poly silicon layer |
| 130 | optical waveguide |
| 133 | reference branch |
| 135 | sensing branch |
| 140 | micro-fluidic components |
| 142 | micromixer |
| 144 | micro-fluidic chamber and channel |
| 150 | SPR sensing area |
| 152 | metal layer |
| 154 | dielectric layer |
| 160 | groove-optical fiber |
| 162 | grove-laser diode |
| 170 | power source |
| 172 | electrodes |
| 174 | battery |
| 180 | optical coupler |
| 190 | driving circuit |
| 241 | fluid inlet |
| 242 | top microfluidic channel |
| 243 | fluid outlet |
| 244 | bottom microfluidic channel |
| 246 | channel interconnection |

The methods, systems, apparatus and devices of the present invention provide a planar integrated optical waveguide type surface plasmon resonance (SPR) sensor. A SPR sensor is the device that measures the changes of refractive index or dielectric constant near the surface of a thin metal layer, resulting from interaction of delocalized electrons in the metal film and photons from an incident light. The metal film is prepared to have a functionalized surface for the adsorption of biochemical molecules. The binding of the molecules changes the refractive index, which is monitored, conventionally, by the absorption peak shift.

Figure 2:
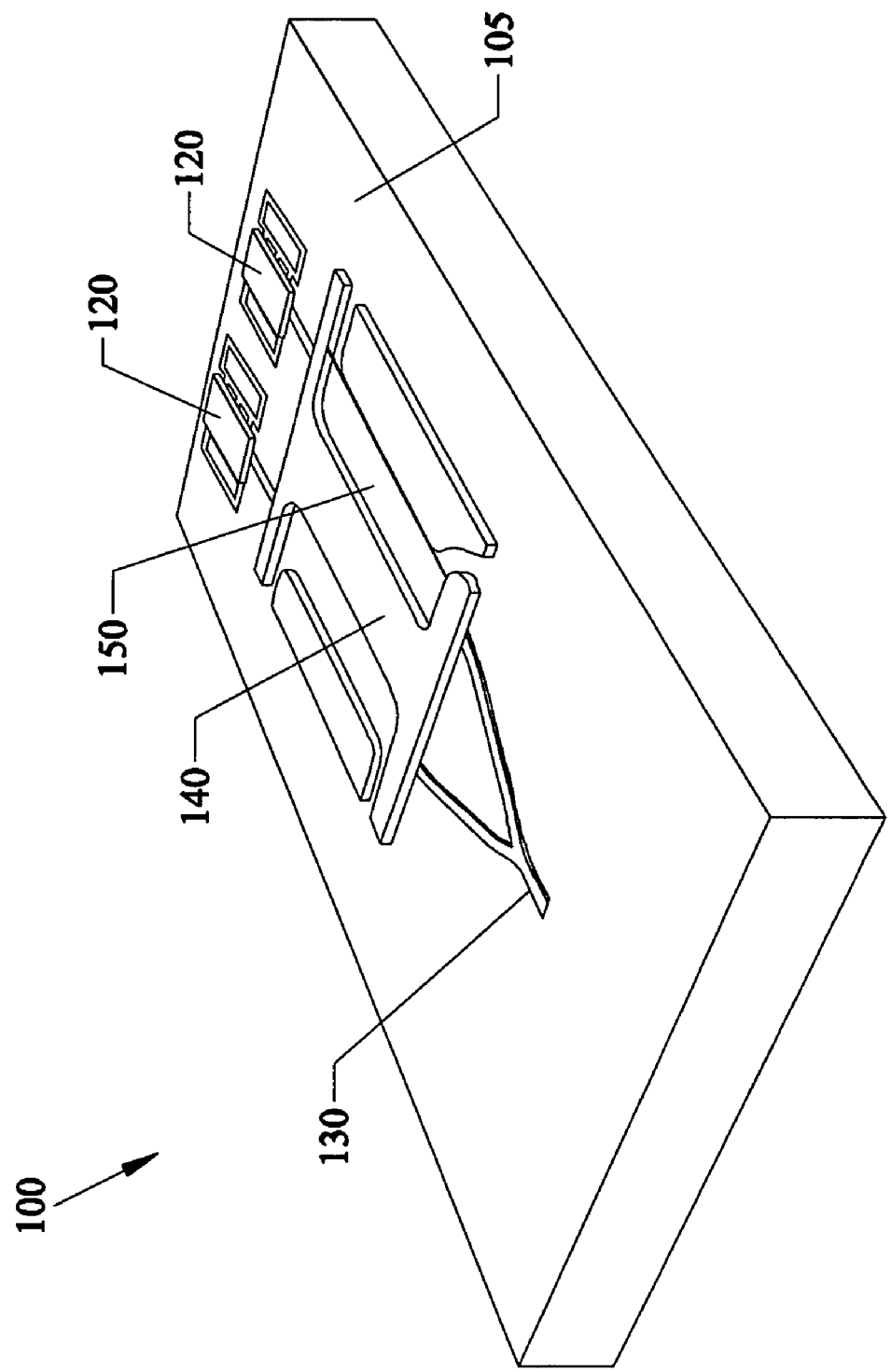
FIG. 2 is a perspective view of a planar integrated optical waveguide type SPR sensor according to an embodiment of the present invention.
Figure 3:
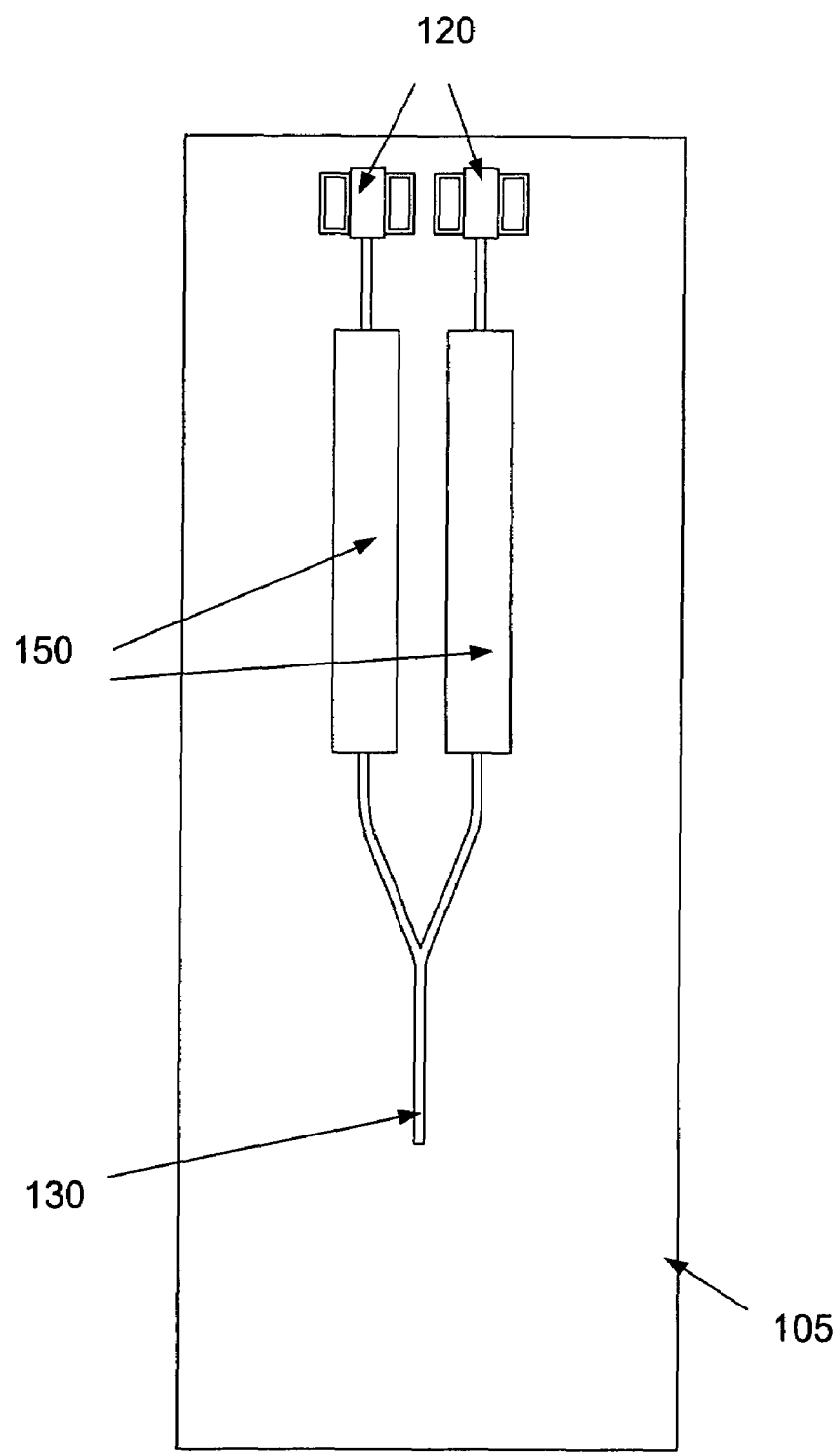
FIG. 3 is a top view of the optical waveguide, overlying SPR sensing area and photodetectors fabricated on the planar substrate.

As shown in FIG. 2, in an embodiment the integrated SPR sensor 100 includes an optical waveguide 130, SPR sensor areas 150 for surface plasmon generation, photodetectors 120, and microfluidic components 140 fabricated on a single substrate 105. FIG. 3 shows a top view of the substrate 105 on which the planar optical waveguide 130 is fabricated. The SPR sensor area 150 is formed to couple with a portion of the planar optical waveguide 130 and the photodetectors 120 are formed to couple with one end of the optical waveguide 130. The other end of the optical waveguide interfaces with a light source. The planar integrated SPR sensor 100 is fabricated on substrate 105 using known technologies from semiconductor production and integrated optics.

The use of the optical waveguides 130 in the integrated SPR sensor 100 provides a simple way to control the optical path in the sensor system including efficient control of properties of the light and suppression of the effect of stray light. Integrating the optical waveguide 130, the SPR sensor areas 150 and the photodetectors 120 on a single planar substrate 105 also reduces the size of the integrated SPR sensor 100 and allows for batch production.

Functionally, a light wave is guided by the optical waveguide and, entering the region with the SPR sensor area, it evanescently penetrates through the SPR sensor area. If the surface plasmon wavelength and the guided mode are phase-matched, the light source excites the surface plasmon at the outer surface of the SPR sensor area and is absorbed.

Figure 4:
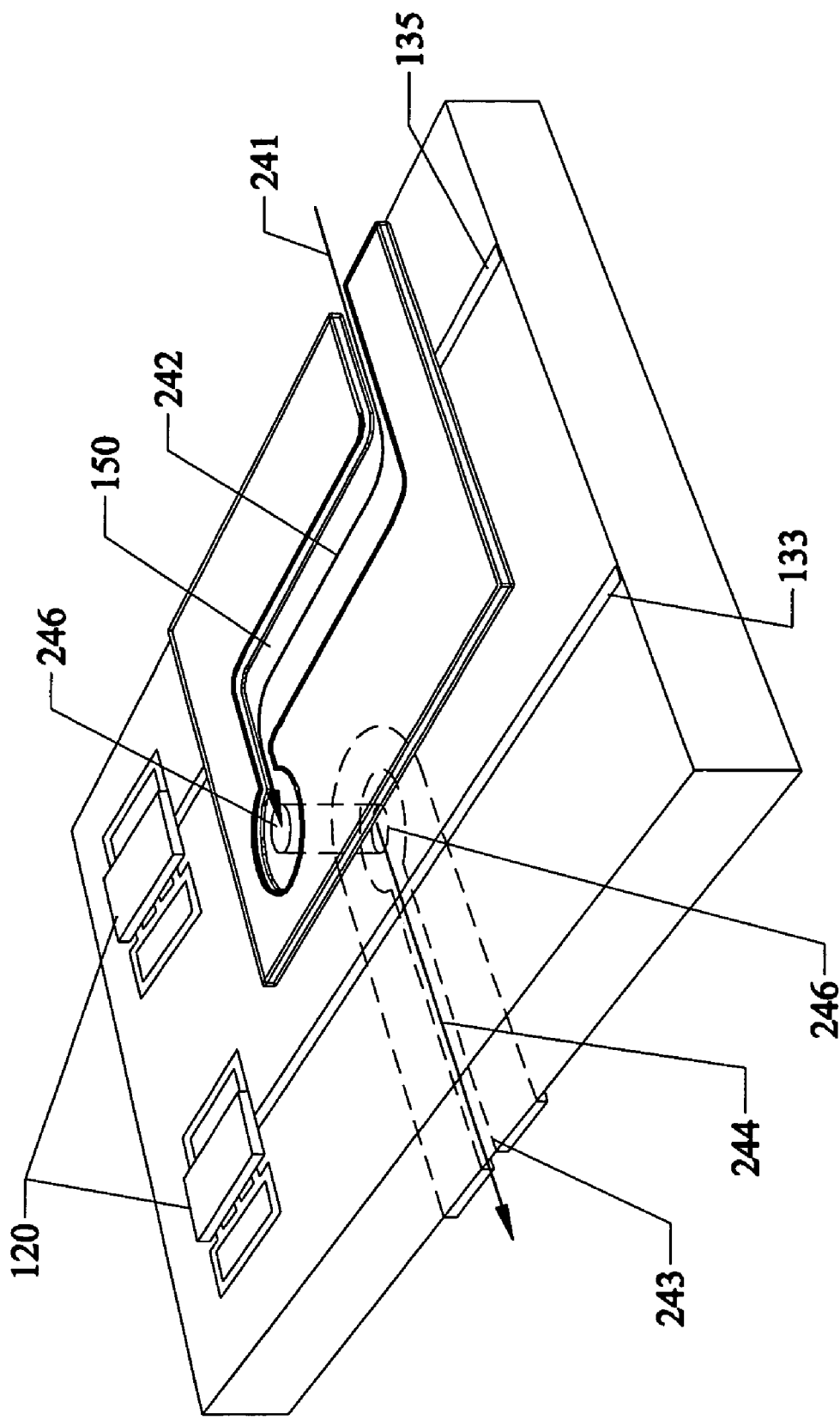
FIG. 4 is a perspective view of the microfluidic structure of the planar integrated optical waveguide type SPR sensor showing a reference branch and a sensing branch.

The planar integrated SPR sensor 100 optionally includes an integrated microfluidic structure 140. The microfluidic structure 140 is fabricated on a two-dimensional flat surface of the substrate 105 as shown in FIGS. 12a through 12d, using interconnections 246 for coupling between the top and bottom fluidic channels 242 and 244, respectively. FIG. 4 shows a section of the integrated SPR sensor microfluidic components fabricated on the substrate 105 in relation to the optical waveguide 130 and the photodetectors 120. As shown, the microfluidic components include a top microfluidic channel 242, a bottom microfluidic channel 244 and a microfluidic channel interconnection 246 for routing the target sample from the top channel 242 to the bottom channel 244. The top microfluidic structure 242 brings the target sample in contact with the SPR sensor area in the sensing branch 135 while the bottom microfluidic structure 244 routes the target sample to contact another SPR sensor (not shown) in the reference branch 133.

An inlet 241 is provided for receiving the target sample which after flowing into and through the bottom microfluidic channel 244, is extracted through outlet 243. The arrows indicate the flow of the target sample into the top microfluidic channel 242, through an interconnection 246 to the bottom microfluidic channel 244 and out of the bottom microfluidic channel 244 outlet 243. The fluidic channels shown in FIG. 4 are for illustration, alternative configurations of the microfluidic channels will be obvious to those skilled in the art.

Figure 5A:
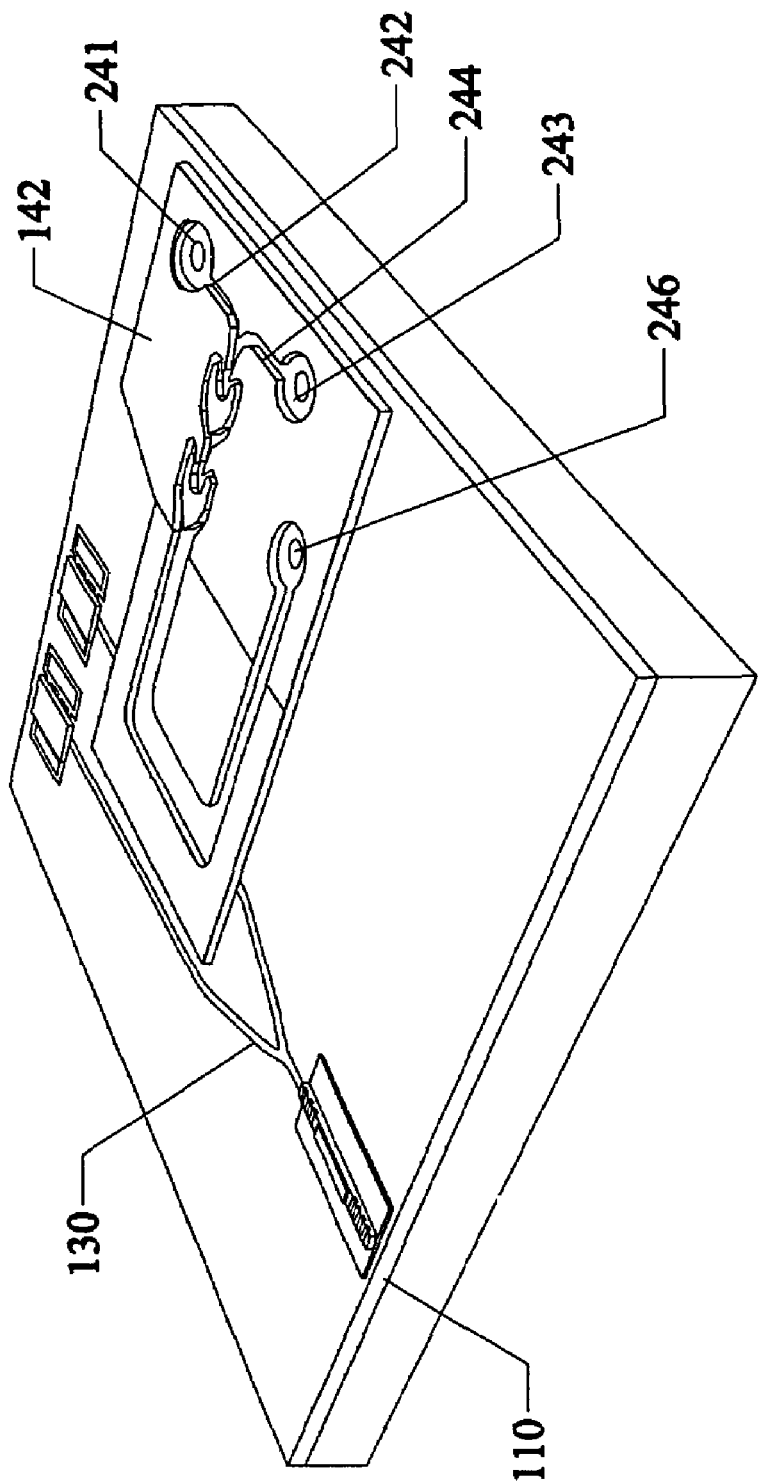
FIGS. 5a and 5b are perspective views of the microfluidic system fabricated and integrated on a planar surface wherein the optical waveguide is coupled with a semiconductor laser and an optical coupler, respectively.
Figure 5B:
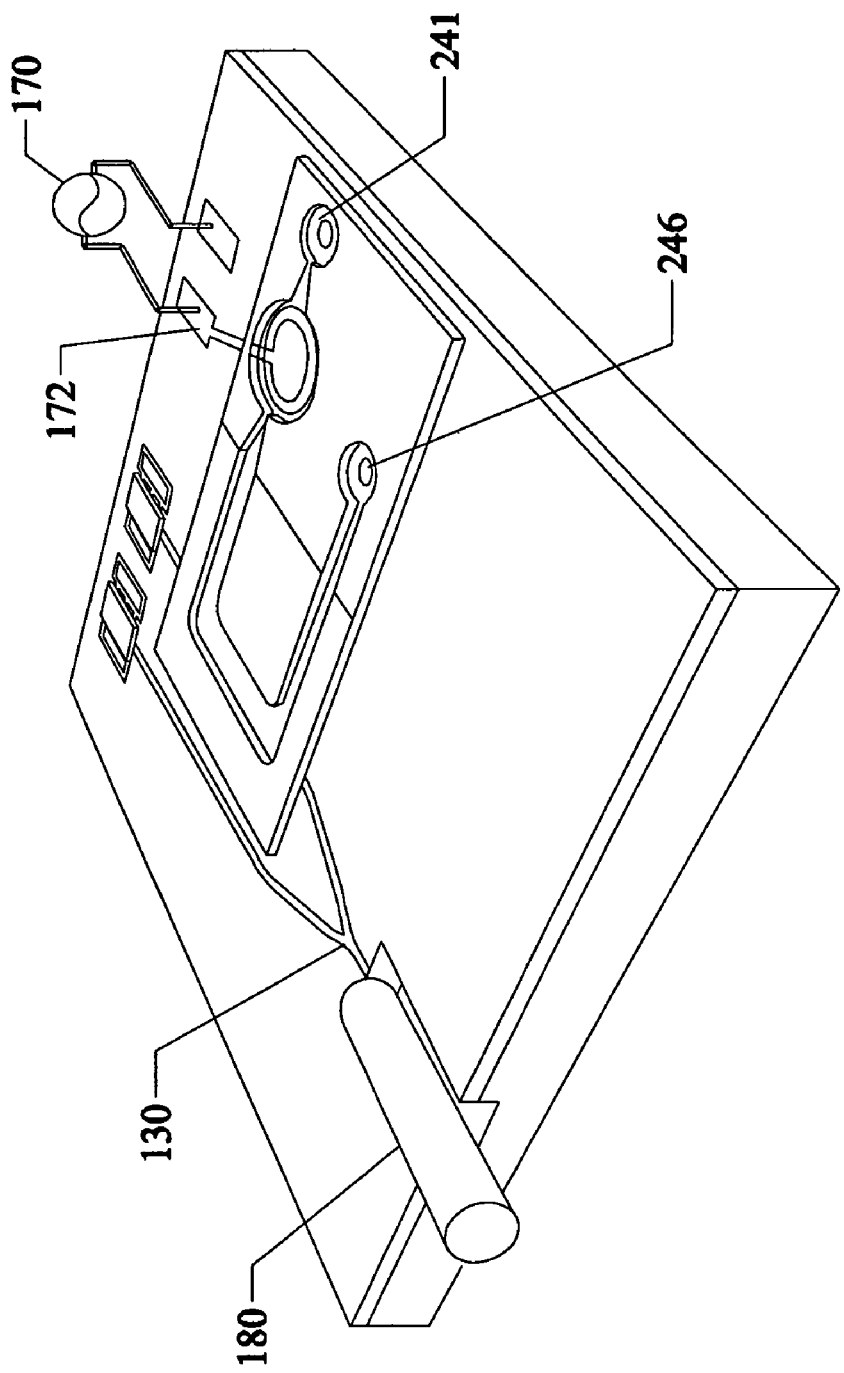

In an alternative embodiment shown in FIGS. 5a and 5b, the planar integrated optical waveguide SPR sensor includes a microfluidic channel network and an optical waveguide coupled with a semiconductor laser 110 and an optical coupler 180, respectively. The microfluidic channel network includes microfluidic components such as a microfluidic reaction chamber, and top and bottom channels 242 and 244, respectively, and a power source as shown in FIG. 5b and alternatively includes a microfluidic mixer 142 as shown in FIG. 5a. Target samples are driven from external pumping sources or, alternatively, micro pumps are integrated into the microfluidic structure.

Microfluidic channels are used as a conduit for the sample introduction and inlets 241, outlets 243 and interconnections 246 are used for routing the sample solutions to overcome 2-dimensional confinement and to allow flexibility in fluidic configuration. The optional reaction chambers are used for biological or chemical reactions while the optional micro mixers allow mixing of different biological or chemical samples. The micro pumps are used to deliver the sample solutions to the reaction chambers and over the optical sensing elements. Microfluidic components facilitate sample handling at the small scale while providing capability of sampling multiple assays and increases accuracy in the sample analysis.

Figure 6:
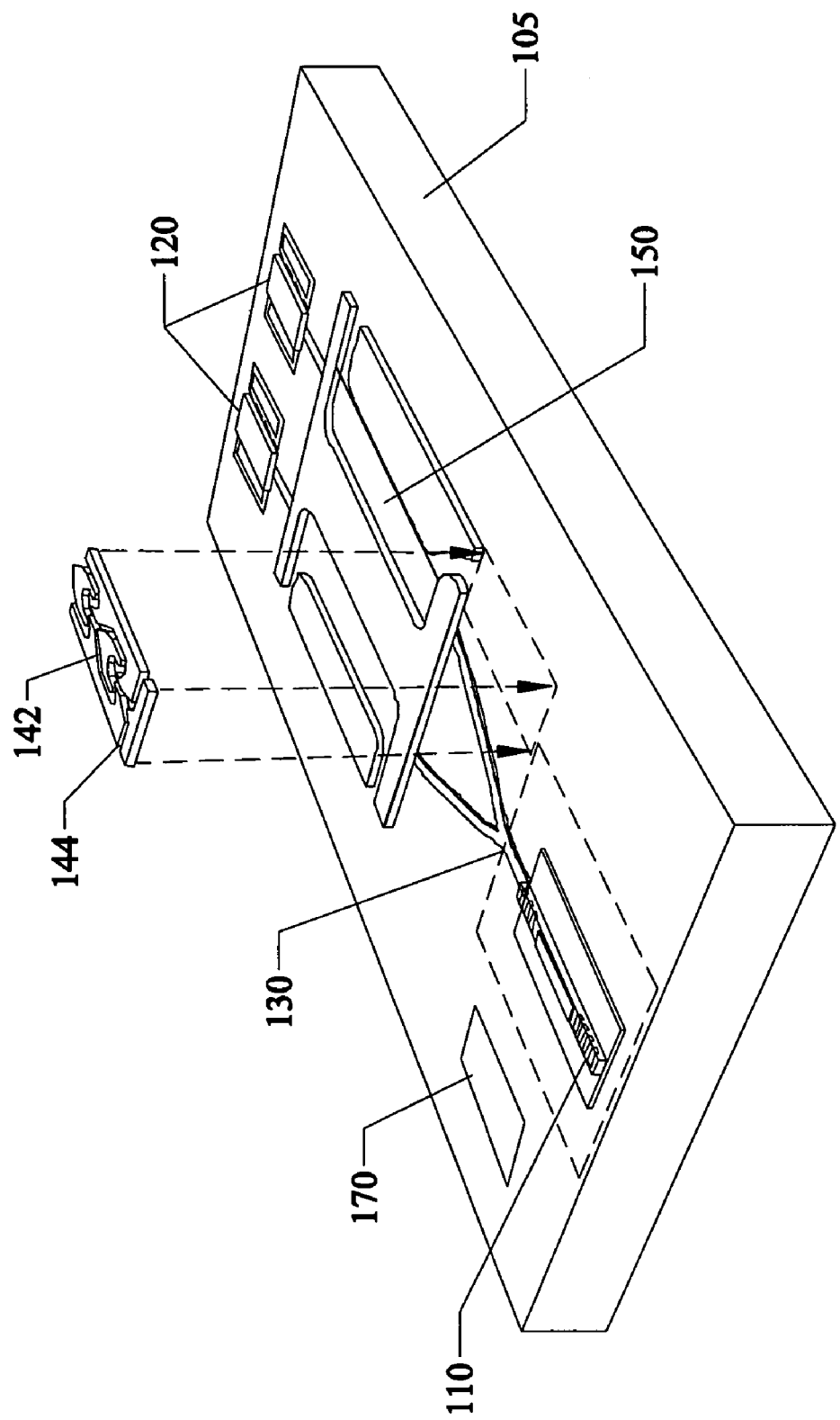
FIG. 6 is a perspective view of alternative configuration of the planar integrated optical waveguide type SPR with optional microfluidic components.

In the embodiment shown in FIG. 6, the integrated SPR sensor 100 includes a semiconductor laser 110, such as a traditional edge-emitting semiconductor laser, in the optical system. The planar optical waveguide 130 couples the laser light to the SPR sensor area 150 that operates on the measuring principle of the surface plasmon resonance in order to measure the target sample brought into contact with the SPR sensing area 150.

The semiconductor laser 110 is fabricated on the substrate 105 using known technologies along with the aforementioned components to allow the design and manufacture of a micro planar integrated SPR sensor. The main advantage of the integrated semiconductor laser is the fixed positioning of the light source relative to the planar optical waveguide, this eliminates the alignment problems associated with the prior art SPR sensors.

Alternatively, the integrated SPR sensor uses a wavelength tunable laser to obtain an absorption spectrum of the transmitted light and detect variations of refractive index by monitoring changes in the frequency corresponding to the maximum absorption. The use of wavelength tunable light source is essential for the operation of the integrated SPR sensor in this embodiment. Basically the SPR sensor is the combination of metal coated sensor head and a spectrometer for the analysis of modulated spectrum of the light from the sensor head. The tunable laser and photodetector combination functions as a spectrometer in this embodiment of the integrated SPR sensor of the present invention.

The tunable laser can be a current controlled tunable laser or other kinds of tunable laser. For example, distributed Bragg reflector (DBR) laser diode is fabricated by conventional semiconductor optoelectronic device manufacturing methods. In the case of Bragg grating based tunable laser, wavelength tuning can be realized by separately applying currents to the grating and non-grating sections. The current applied to the grating sections tunes the wavelength of operation while other current maintains optical gain for laser action. The integrated SPR sensor 100 includes a power source 170 as shown in FIG. 6, or other means for providing a driving current for use by the tunable laser and a bias voltage for the photodetectors.

Figure 7:
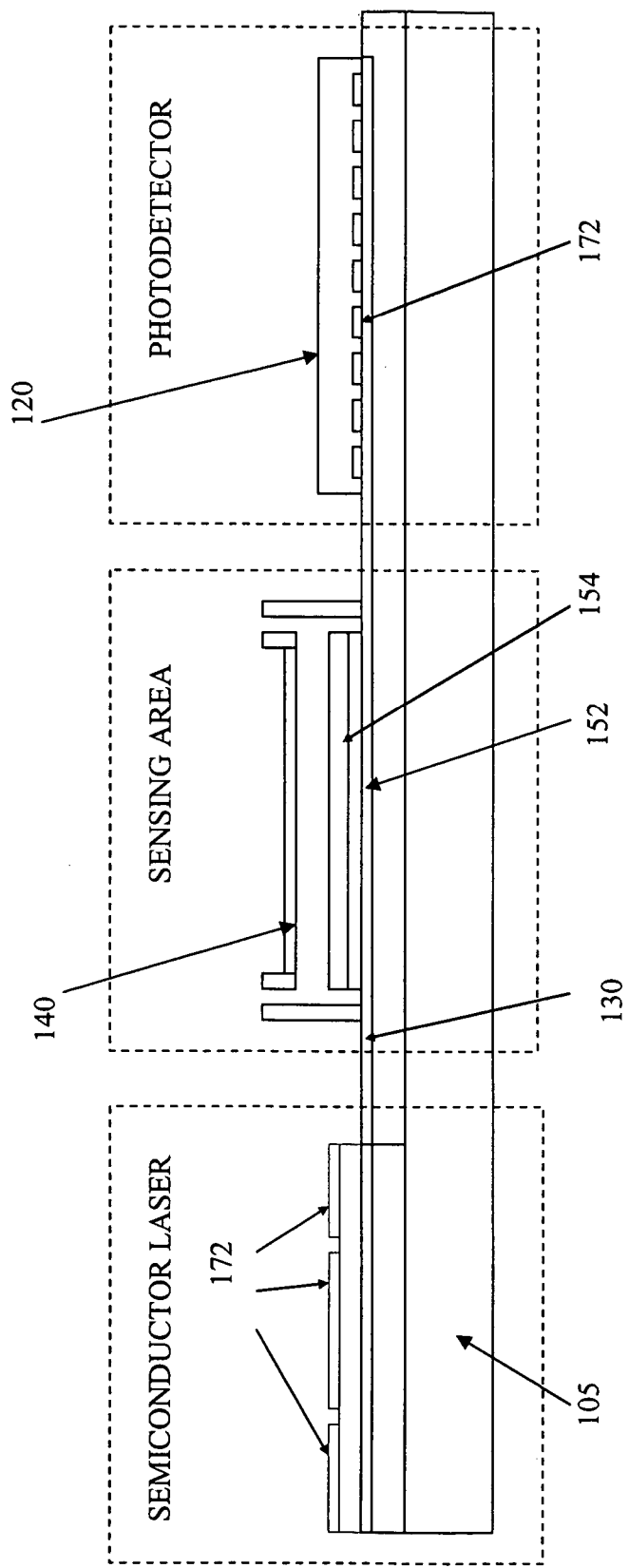
FIG. 7 is side view of the planar integrated optical waveguide type SPR sensor shown in FIG. 6.

FIG. 7 is a side view of the planar integrated optical waveguide SPR sensor of FIG. 6 showing the substrate 105 and the components fabricated on the substrate 105. The side view is divided into three sections showing fabrication of the wavelength tunable laser in the left section, the SPR sensing area in the center section and the photodetector in the section on the right. As shown, the waveguide 130 couples with the wavelength tunable laser at one end and with the photodetector at the opposite end. The SPR sensor area includes a thin metal layer 152 formed over a section of the optical waveguide 130 and a dielectric layer 154 deposited on the thin metal layer 152. The photodetector and the wavelength tunable laser sections include electrodes 172 for receiving a driving current to power these wavelength tunable type devices.

Figure 11F:
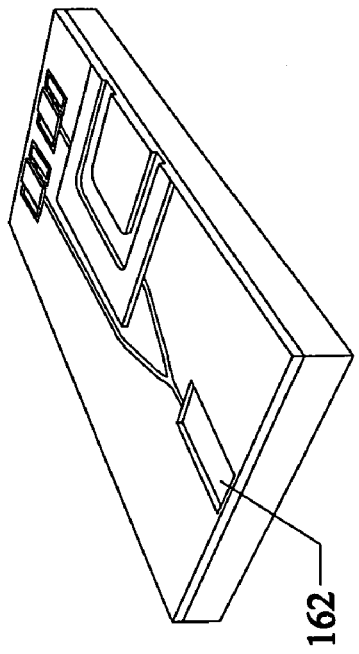

FIGS. 11a through 11i show an example of fabrication steps for the integrated SPR sensor of the preferred embodiment. However, the fabrication steps and materials may be changed depending on the device structural requirements. On silicon or GaAs substrate 105, $SiO_2$ and SiON layers 106 and 107, respectively, are deposited (FIG. 11a) and by reactive ion etching, the optical waveguide 130 is patterned as shown in FIG. 11b. Metallic film such as gold is deposited and pattered for the SPR sensor head 150 over a section of the optical waveguide 130 and for the electrodes 172 for photodetector at one end of the optical waveguide 130 as shown in FIG. 11c. Alternatively, optical waveguide 130 is formed using photosensitive polymers such as SU-8 without reactive ion etching step.

Figure 11G:
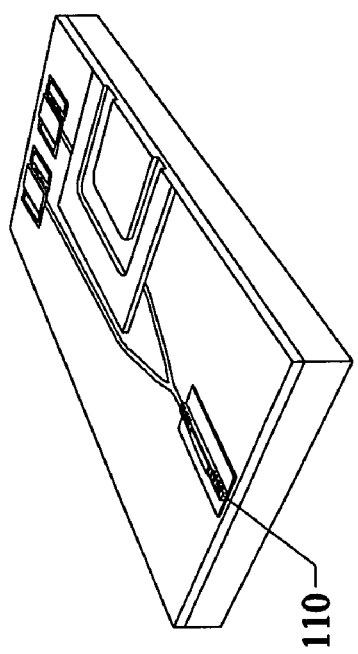
Figure 11H:
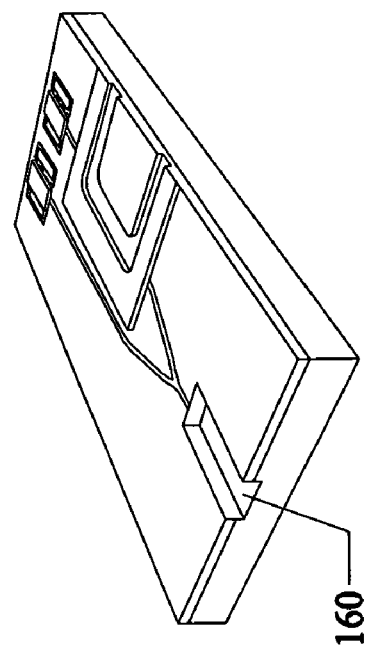
Figure 11I:
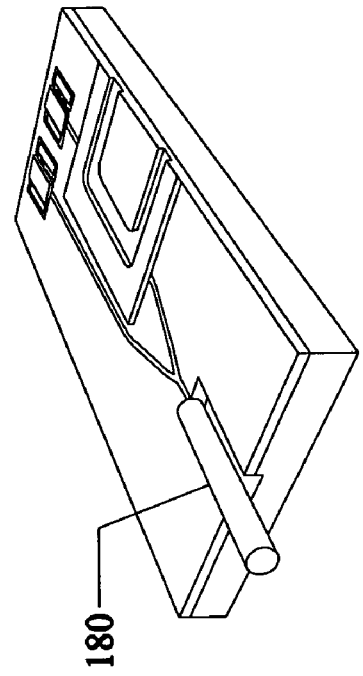
Figure 12B:
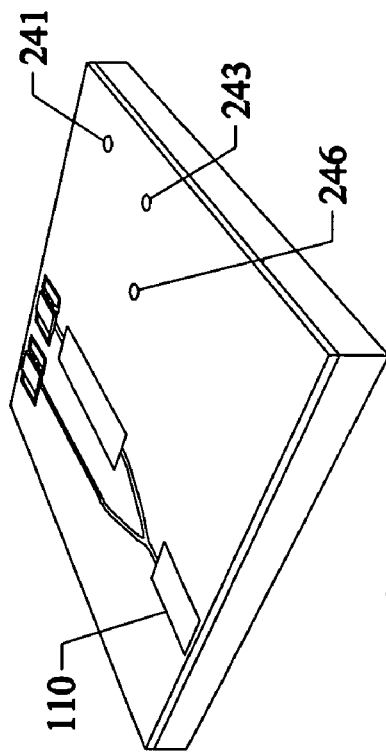
FIGS. 12a-12d are perspective views of the planar integrated optical waveguide type SPR sensor at different steps of an alternative fabrication process.
Figure 12D:
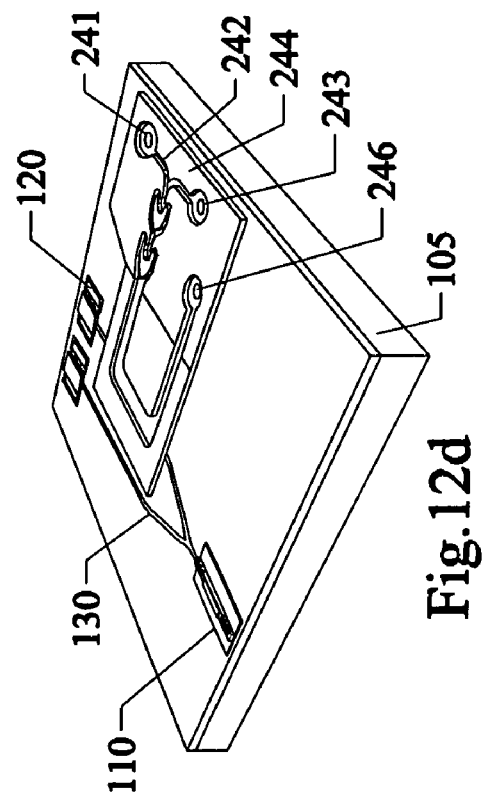
Figure 12A:
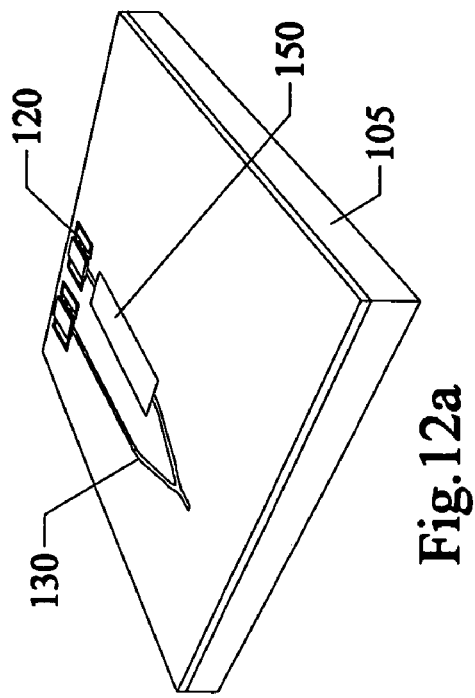
Figure 12C:
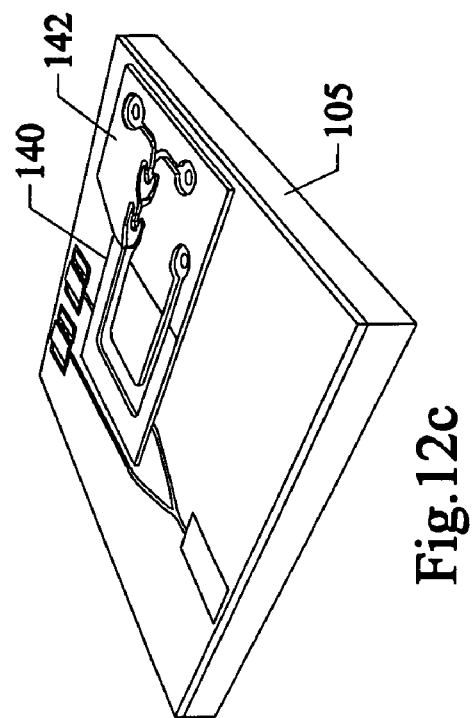

Polysilicon 122 is deposited over the electrodes 172 as shown in FIG. 11d to make the photodetectors. As shown in FIG. 11e, microfluidic components 140 are made of photosensitive polymers such as SU-8 for routing the target sample into contact with the SPR sensor head 150. Depending on the final configuration, different steps are taken. For optical fiber coupling type devices (FIGS. 11f and 11g), reactive ion etching is performed to make a groove 160 which is used as an optical coupler. Finally, the optical fiber 180 is inserted into the groove 160 as shown in FIG. 11g, forming the optical coupler. As shown in FIG. 11h, for the laser diode integrated type of SPR sensors, reactive ion etching is performed to make a groove 162 for hybrid assembly or embedding of tunable laser diode 110 which is integrated into the substrate 105.

Figure 8:
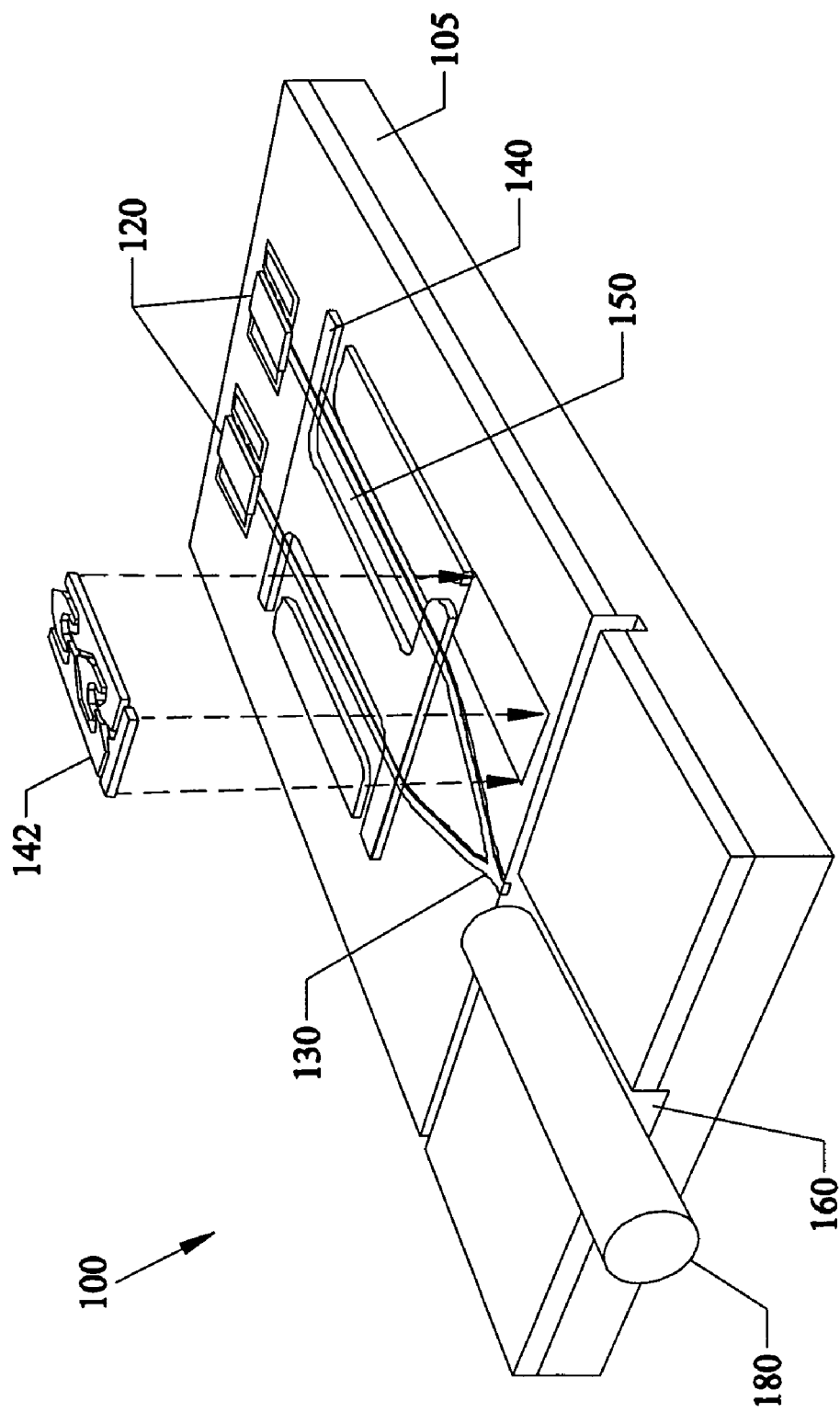
FIG. 8 is a perspective view of an alternative configuration of the planar integrated optical waveguide type SPR sensor with an optical coupler light source.
Figure 9:
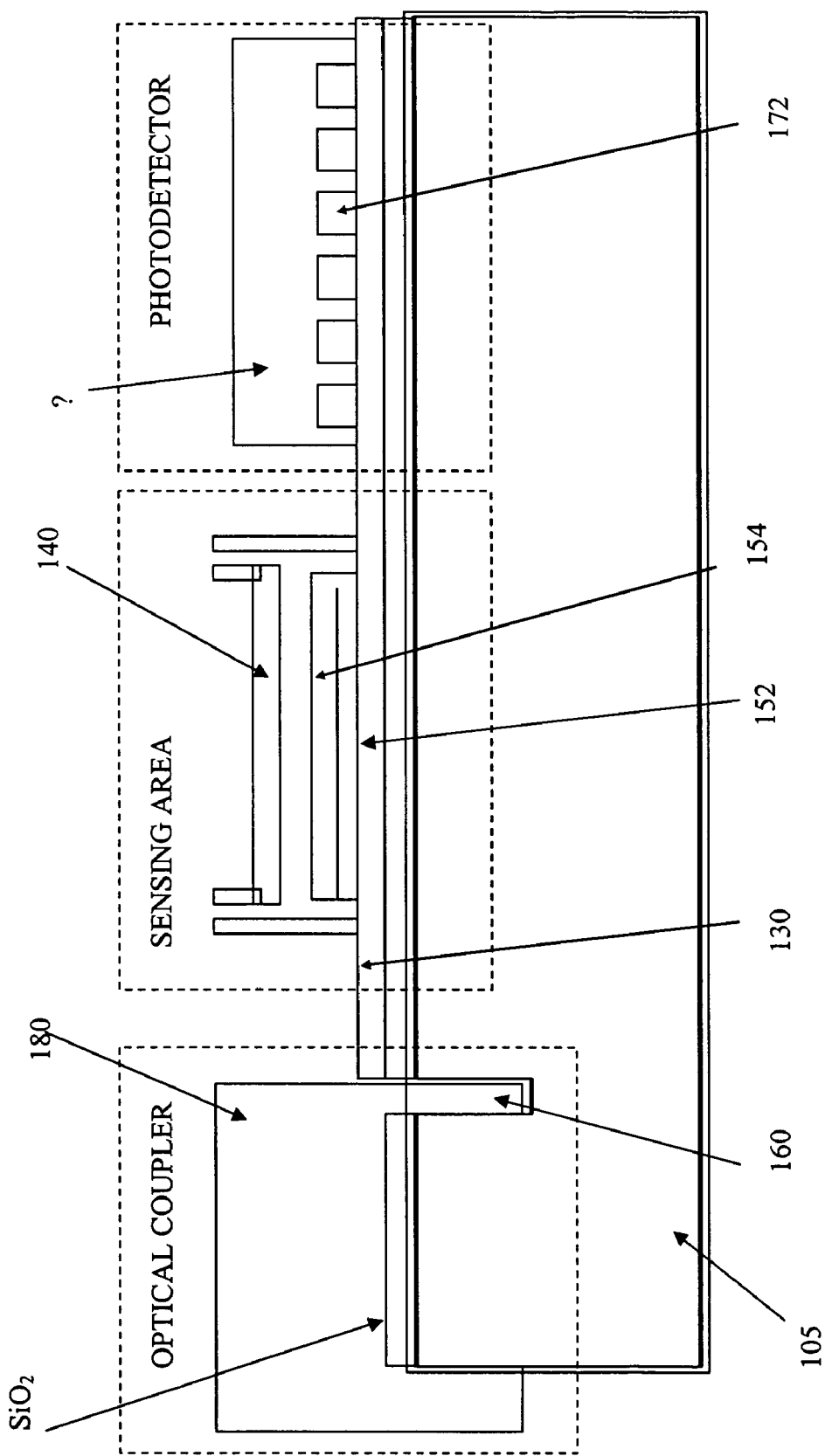
FIG. 9 is side view of the optical coupler, the SPR sensor and the photodetector of the planar integrated optical waveguide type SPR shown in FIG. 8.

In the configuration shown in FIG. 8, the planar integrated optical waveguide SPR sensor 100 includes an optical fiber 180 for coupling the light from an external light source (not shown). The integrated SPR sensor 100 in this embodiment includes a channel 160 formed in the substrate 105 and overlaying layers for coupling the optical fiber 180 with the optical waveguide 130. FIG. 9 is a side view of the configuration shown in FIG. 8 divided into three sections. From left to right, the first section shows the coupling of the optical fiber 180 with the optical waveguide 130, the center section shows the sensing area of the planar device and the right section shows the photodetector, all of which are fabricated on the planar substrate 105.

As previously described for the embodiment shown in FIG. 6, the optical waveguide 130 is formed on the substrate 105 and the corresponding SPR sensor area 150 is fabricated by forming the thin metal layer 152 on an area of the optical waveguide 150 and applying the dielectric layer 154 over the thin metal layer. The photodetector section shown on the right illustrates fabrication of photodetector 120 on the planar substrate 105 following the same process as previously described in regard to FIGS. 11c and 11d and as shown in FIGS. 11f and 11g, physical confinement of the optical fiber 180 is realized with groove 160 made by reactive ion etching wherein the optical fiber 180 fits into the groove 160.

Figure 10:
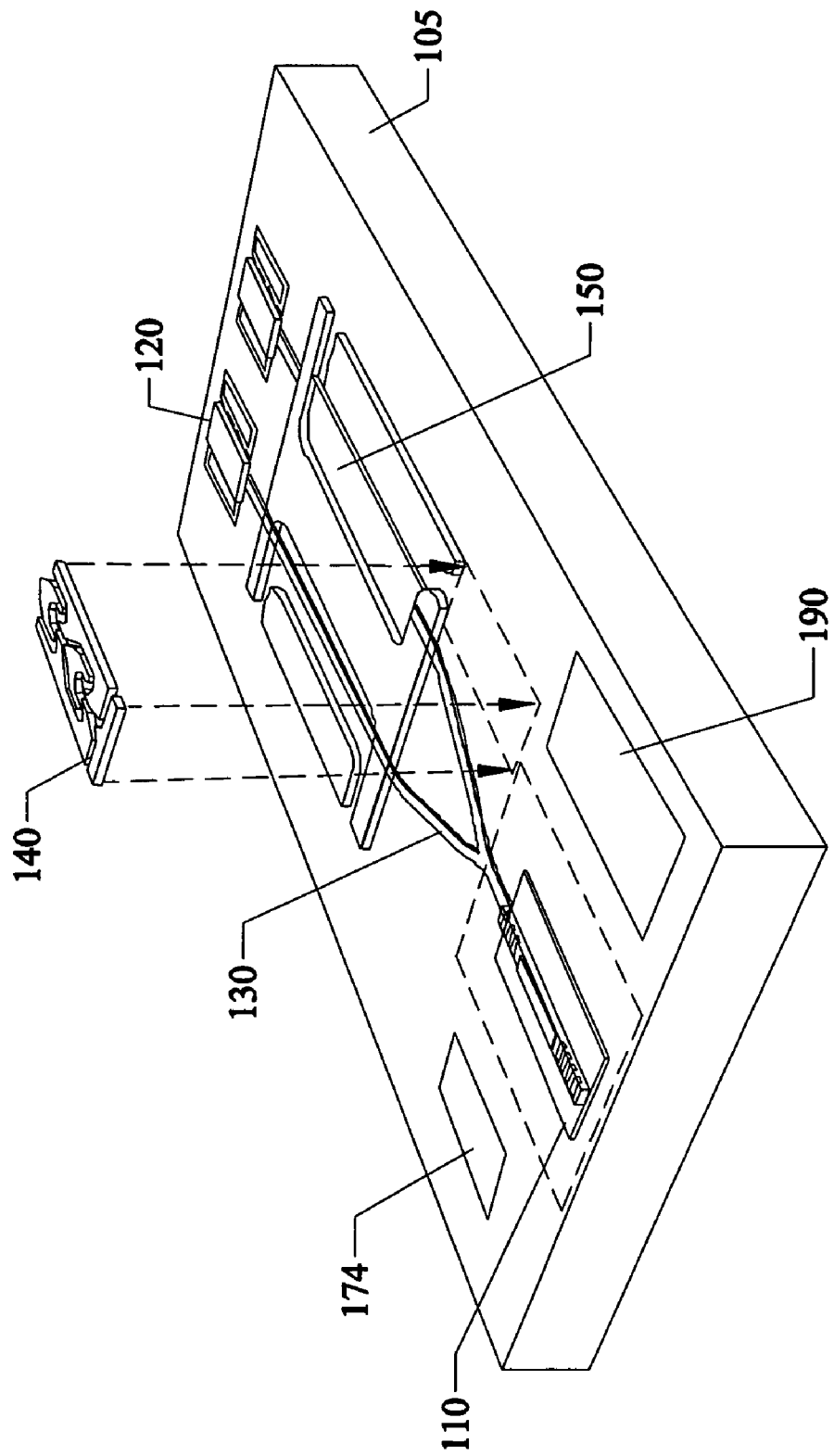
FIG. 10 is a perspective view of an alternative configuration of the planar integrated optical waveguide type SPR sensor with an integrated semiconductor laser light source.

Alternatively, as shown in FIG. 10, the integrated waveguide type SPR sensor includes a driving circuit 190 coupled with the substrate 105 for controlling the semiconductor laser 110 and the photodetectors 120. The integrated SPR sensor may also include a power source or an interface for supplying power to the integrated SPR sensor as shown in FIG. 6 or a battery 174 as shown in FIG. 10. The driving circuit may include a means for communicating via a variety of communication formats or may include integrated components such as a microprocessor based controller with memory and a user interface.

Combined integration of the driving circuits and the interconnected fluidic components with the SPR sensor enable a planar on-chip integrated waveguide type SPR sensor which reduces the size of the instruments incorporating the integrated device. Using standard IC fabrication techniques, electronic circuits for controlling wavelength and analysis of acquired signals can be fabricated on the substrate where the SPR sensor shares the same substrate and is made by the compatible micro fabrication process. Integration of components on a single substrate reduces the whole system into a chip size.

In an alternative embodiment, plural optical waveguide type SPR sensors are integrated on a single substrate, each sensor including a light source, waveguide and corresponding SPR sensor area and photodetector. In this embodiment of the invention, plural optical waveguides and corresponding SPR sensor areas may be arranged in parallel and simultaneously brought into contact with one or more target samples. The array of sensors in this embodiment may also include at least one fluidic structure. As previously described, the fluidic structure may include a fluidic channel, a micromixer and a fluidic reaction chamber. Alternatively, multiple optical waveguide type SPR sensors with various target analytes may be formed into an array to monitor multiple biological or chemical reactions simultaneously.

In this alternative embodiment, the multiple micro integrated optical waveguide SPR sensors interface with one another to form an array, however, they are not directly interfaced with one another. Instead, the individual SPR sensors are designed for specific target molecules or cells and the multiple SPR sensors are used to detect a variety of different target samples. For example, multiple strains of a virus, types 1, 2 and 2, can be detected using the array instead of using individual SPR sensor devices for detecting each type.

In summary, the present invention provides new methods, systems, apparatus and devices for micro fabrication of the SPR sensor components on the substrate which fundamentally advances the sensing technology by reducing the SPR sensor size, eliminating complexity in optical configurations and eliminating the problems associated with using out-of-plane components, such as alignment of the external light source.

The micro integrated SPR sensor includes an optical waveguide and corresponding SPR sensor area fabricated on a planar substrate. A photodetector formed on the substrate couples with one end of the optical waveguide and a light source is coupled with the other end of the optical waveguide. The light source is one of a wavelength tunable laser formed on the substrate and an optical fiber and corresponding optical coupler for coupling the light to the optical waveguide. In an embodiment, the micro integrated SPR sensor optionally includes a microfluidic structure fabricated on the substrate with the optical waveguide for routing a target sample to the SPR sensor area.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A planar integrated surface plasmon resonance (SPR) sensor comprising:
    a substrate having a first side and a second side;
    an planar optical waveguide fabricated on a surface of the first side of the substrate, the optical waveguide having a first end and a second end;
    a wavelength tunable emitter on a same surface of the substrate coupled with the first end of the optical waveguide wherein the wavelength of the emitted light is varied to obtain a transmission spectrum of light which passes through a sensing region for detecting variations in a refractive index by monitoring a maximum absorption peak shift in a wavelength domain;
    at one single photodetector formed on the same surface of the substrate coupled with the second end of the optical waveguide for measuring a transmitted intensity of light exiting the second end of the planar optical waveguide; and
    at least one SPR sensor area formed on the first side of the substrate to couple with a section of the optical waveguide between the wavelength tunable laser and the one single photodetector, wherein the optical waveguide routes a light from the light source past the at least one SPR sensor area which evanescently penetrates the at least one SPR sensor area.

2. The integrated SPR sensor of claim 1, wherein the at least one SPR sensor area comprises:
    an SPR sensing layer; and
    an analyte selective layer on the SPR sensing layer.

3. The integrated SPR sensor of claim 1, wherein each of the at least one SPR sensor area comprises:
    a metal coated sensor head coupled with the section of the optical waveguide.

4. The integrated SPR sensor of claim 1, wherein the light source comprises:
    a wavelength tunable laser.

5. The integrated SPR sensor of claim 1, wherein the light source comprises:
    an edge-emitting semiconductor laser coupled with the first end of the optical waveguide.

6. The integrated SPR sensor of claim 1, further comprising:
    a power source coupled with the substrate for providing a driving current to the wavelength tunable laser.

7. The integrated SPR sensor of claim 1, further comprising:
    a voltage source coupled with the one single photodetector for providing a bias voltage to the one single photodetector.

8. The integrated SPR sensor of claim 1, further comprising:
    a communication interface coupled with the integrated SPR sensor to allow the integrated SPR sensor to communicate with a user via a communication format.

9. The integrated SPR sensor of claim 1, further comprising:
    a controller for controlling the operation of the integrated SPR sensor.

10. The integrated SPR sensor of claim 1, wherein the planar optical waveguide comprises:
    a sensing branch coupled with a first one of the at least one SPR sensor area, wherein a target sample is routed into contact with the first one of the at least one SPR sensor area; and
    a reference branch coupled with a second one of the at least one SPR sensor area for providing a reference.

11. The integrated SPR sensor of claim 1, further comprising:
    a microfluidic structure having an inlet and an outlet with a channel therebetween fabricated on the substrate for receiving a target sample, routing the target sample into contact with the at least one SPR sensor area and extracting the target sample.

12. The integrated SPR sensor of claim 11, wherein the microfluidic structure comprises:
    at least one of a micro-fluidic reaction chamber, a micro-mixer and a micro pump fabricated on the substrate in connection with the channel.

13. A method for fabricating an integrated optical waveguide type surface plasmon resonance (SPR) sensor, the method comprising the steps of:
    providing a substrate;
    forming a planar optical waveguide on a surface of the substrate, the optical waveguide having a first end and a second end;
    fabricating a wavelength tunable light emitter on a same surface of the substrate coupled with the first end of the planar optical waveguide, wherein the wavelength of emitted light is varied to obtain a transmission spectrum of light which passes through a sensing region for detecting variations in a refractive index by monitoring a maximum absorption peak shift in a wavelength domain;
    forming a SPR sensor on the same surface of the substrate in contact with a section of the planar optical waveguide between the first end and the second end;
    forming a fluidic structure on the substrate to route a target sample past the SPR sensor; and forming one single photodetector on the same surface of the substrate coupled with the second end of the planar optical waveguide, the tunable light emitter and photodetector combination functioning as a spectrometer.

14. The method of claim 13, wherein the fabricating a wavelength tunable light emitter comprises the step of:

fabricating a wavelength tunable laser on the substrate, the wavelength tunable laser output coupled with the first end of the optical waveguide.

15. The method of claim 14 further comprising the step of:

fabricating a power source on the substrate for supplying a current to the wavelength tunable laser and a bias voltage to the one single photodetectors.

16. The method of claim 13, further comprising the step of:

forming an optical coupler on the substrate to allow an optical fiber to couple a light to the first end of the optical waveguide.

17. The method of claim 13, further comprising the step of:

forming a communication interface on the substrate for communication with the integrated SPR sensor during operation.

18. The method of claim 13, wherein the step of forming a fluidic structure comprises the steps of:

forming an inlet and an outlet in the substrate for the introduction and extraction of the target sample from the integrated SPR sensor; and forming at least one channel between the inlet and the outlet for routing the target sample past the SPR sensor area.

19. The method of claim 18, further comprising the step of:

forming at least one of a microfluidic mixture and an optional microfluidic reaction chamber coupled with the at least one channel on the substrate for mixing of different biological and chemical samples and allowing biological and chemical reactions, respectively, to occur, wherein the fluidic structure facilitates sample handling at a small scale while providing capability of multiple assays and accuracy in sample analysis.

20. The method of claim 18, further comprising the step of:

forming a micro pump on the substrate coupled with the fluidic structure to route the target sample between the inlet and the outlet and past the SPR sensor.

21. The method of claim 13, further comprising the step of:

fabricating a controller on the substrate for controlling the operation of the integrated SPR sensor.

\* \* \* \* \*